(12) United States Patent
Wang et al.

(10) Patent No.: US 12,419,956 B2
(45) Date of Patent: Sep. 23, 2025

(54) CONTROLLED DRUG RELEASE SYSTEM OF PHOTORESPONSIVE NANOCARRIERS, METHODS OF MAKING AND USING THEREOF

(71) Applicant: THE UNIVERSITY OF HONG KONG, Hong Kong (CN)

(72) Inventors: Weiping Wang, Hong Kong (CN); Kaiqi Long, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 682 days.

(21) Appl. No.: 17/904,833

(22) PCT Filed: Mar. 17, 2021

(86) PCT No.: PCT/CN2021/081262
§ 371 (c)(1),
(2) Date: Aug. 23, 2022

(87) PCT Pub. No.: WO2021/213089
PCT Pub. Date: Oct. 28, 2021

(65) Prior Publication Data
US 2023/0124487 A1    Apr. 20, 2023

Related U.S. Application Data

(60) Provisional application No. 63/014,954, filed on Apr. 24, 2020.

(51) Int. Cl.
| | | |
|---|---|---|
| *A61K 47/22* | (2006.01) | |
| *A61K 9/51* | (2006.01) | |
| *A61K 31/337* | (2006.01) | |
| *A61K 31/704* | (2006.01) | |
| *A61K 31/7068* | (2006.01) | |
| *A61K 41/00* | (2020.01) | |
| *A61N 5/06* | (2006.01) | |
| *A61P 27/16* | (2006.01) | |
| *A61P 35/00* | (2006.01) | |
| *C07D 311/58* | (2006.01) | |

(52) U.S. Cl.
CPC ........ *A61K 41/0042* (2013.01); *A61K 9/5123* (2013.01); *A61K 31/337* (2013.01); *A61K 31/704* (2013.01); *A61K 31/7068* (2013.01); *A61N 5/062* (2013.01); *A61P 27/16* (2018.01); *A61P 35/00* (2018.01); *C07D 311/58* (2013.01); *A61N 2005/0651* (2013.01); *A61N 2005/0659* (2013.01); *A61N 2005/0663* (2013.01)

(58) Field of Classification Search
CPC .............. A61K 41/0042; A61K 9/5123; A61K 31/337; A61K 31/704; A61K 31/7068; A61K 9/0019; A61K 9/51; A61N 5/062; A61N 2005/0651; A61N 2005/0659; A61N 2005/0663; A61P 27/16; A61P 35/00; C07D 311/58
See application file for complete search history.

(56) References Cited

U.S. PATENT DOCUMENTS 9,700,620 B2   7/2017   Almutairi et al.

FOREIGN PATENT DOCUMENTS

WO    2011130114 A1   10/2011

OTHER PUBLICATIONS

Gandioso, A. et al., "Sequential uncaging with green light can be achieved by fine-tuning the structure of a dicyanocoumarin chromophore.", Chemistry Open.,vol. 6, No. 3, May 5, 2017 (May 5, 2017).
Fournier, L. et al., "Coumarinylmethyl caging groups with redshifted absorption.", Chemistry European Journal.,vol. 19, No. 51, Dec. 16, 2013 (Dec. 16, 2013).
Wang, W. et al., "Self-assembly mediated platform for rapid and facile preparation of peptide-functionalized nanoparticles with high stability.", Chemistry of Materials.,vol. 24, No. 5, Dec. 6, 2011.
Yamazoe, S. et al., "Sequential gene silencing using wavelength-selective caged morpholino bligonucleotides.", Angewandte Chemie International Edition.,vol. 53, No. 38, Sep. 15, 2014.
Zhang, Y. J. et al., "Cationic polythiophenes as gene delivery enhancer.", ACS applied materials & interfaces.,vol. 9, No. 20, May 11, 2017 (May 11, 2017).
Gandioso, A. et al., "A green light-triggerable RGD peptide for photocontrolled targeted drug delivery: synthesis and photolysis studies.", The Journal of organic chemistry.,vol. 81, No. 23, 09.
Jin, Y. et al., "Synthesis and self-assembly of nonamphiphilic hyperbranched polyoximes.", Soft Matter.,vol. 8, No. 39, Jul. 24, 2012 (Jul. 24, 2012).
Rehm, T. H. et al., "Self-assembly of a triple-zwitterion in polar solutions: hierarchical formation of nanostructures.", Soft Matter.,vol. 8, No. 11, Feb. 7, 2012 (Feb. 7, 2012).
Wang, W. et al., "Efficient and facile formation of two-component nanoparticles via aromatic moiety directed self-assembly.", Chemical communications.,vol. 47, No. 37, Apr. 26, 2011 (Apr. 26, 2011).
Long, K. et al., "Self-assembly of trigonal building blocks into nanostructures: molecular design and biomedical applications.", Journal of Materials Chemistry B.,vol. 8, No. 31, Jul. 20, 2020.
Yafei Li, Yaming Zhang, and Weiping Wang, "Phototriggered targeting of nanocarriers for drug delivery", Nano Research, 2018, 11 (10),5424-5438.
S. Stolik et al., "Measurement of the penetration depths of red and near infrared light in human "ex vivo" tissues", Journal of Photochemistry and Photobiology B: Biology, 2000, 57 90-93.
Weiping Wang and Ying Chau, "Efficient and facile formation of two-component nanoparticles via aromatic moiety directed self-assembly", Chem. Commun., 2011, 47 (37), 10224-10226.

(Continued)

*Primary Examiner* — Jessica Worsham
(74) *Attorney, Agent, or Firm* — LEASON ELLIS LLP

(57) ABSTRACT

Disclosed herein is a controlled drug release system of photoresponsive nanocarriers. Also provided are methods of making the nanocarriers. Also provided are method of using the nanocarriers for the treatment of diseases.

22 Claims, 9 Drawing Sheets

(56) References Cited

OTHER PUBLICATIONS

Figure 1:
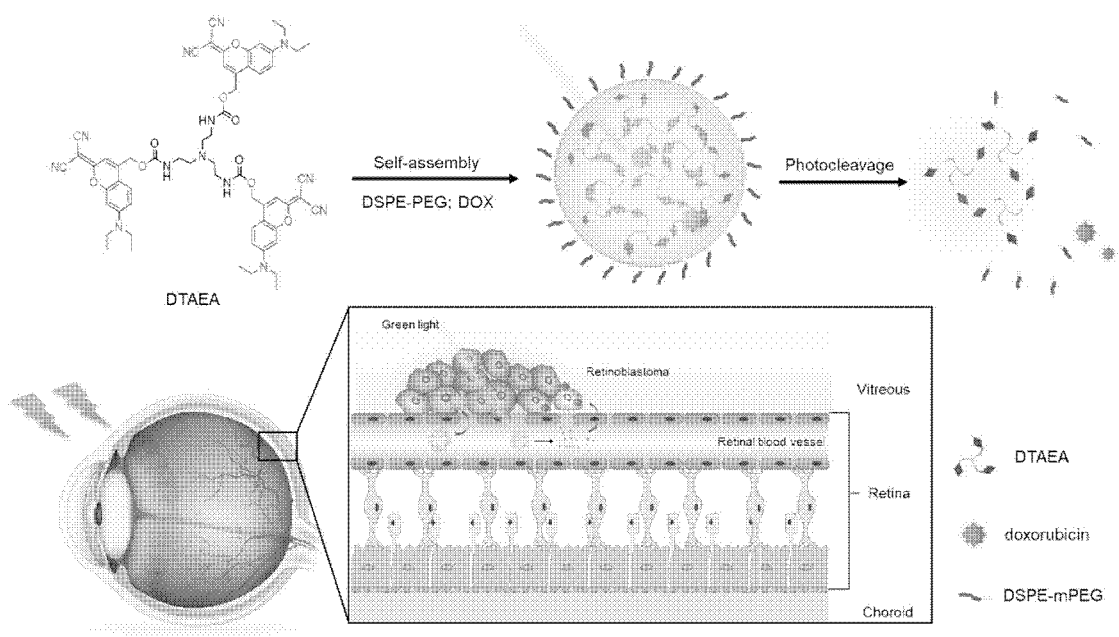
Figure 1:
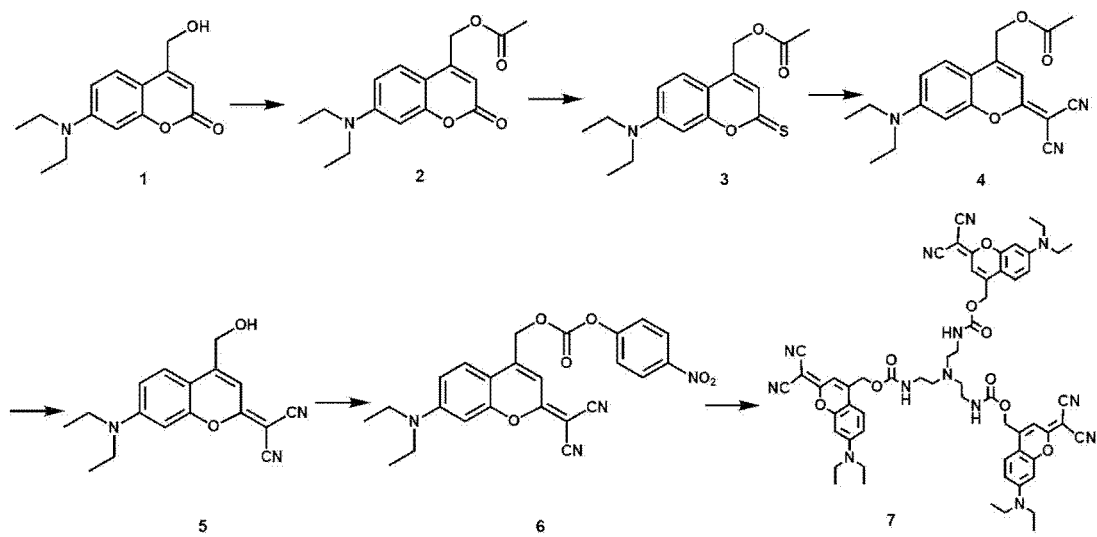

Weiping Wang and Ying Chau, "Self-Assembly Mediated Platform for Rapid and Facile Preparation of Peptide-Functionalized Nanoparticles with High Stability", Chem. Mater., 2012, 24 (5), 946-953.
Alina Y. Rwei et al, "Photoresponsive nanoparticles for drug delivery", Nano Today, 2015, 10 (4), 451-467.
Shields Carol et al., "Targeted retinoblastoma management: when to use intravenous, intra-arterial, periocular, and intravitreal chemotherapy", Current Opinion in Ophthalmology, 2014, 25 (5), 374-385.
Yanfei Wang et al., "Intravenous treatment of choroidal neovascularization by photo-targeted nanoparticles", Nature Comm., 2019,10, 804.
Albert Gandioso et al., "Sequential Uncaging with Green Light can be Achieved by Fine-Tuning the Structure of a Dicyanocoumarin Chromophore", ChemistryOpen, 2017, 6, 375-384.
Ji-Young Kim et al., "The use of PEGylated liposomes to prolong circulation lifetimes of tissue plasminogen activator", Biomaterials, 2009, 30, 5751-5756.
Viet Anh Nguyen Huu et al., "Light-responsive nanoparticle depot to control release of a small molecule angiogenesis inhibitor in the posterior segment of the eye", Journal of Controlled Release, 2015, 200, 71-77.

Scheme 1

CONTROLLED DRUG RELEASE SYSTEM OF PHOTORESPONSIVE NANOCARRIERS, METHODS OF MAKING AND USING THEREOF

CROSS-REFERENCE TO RELATED PATENT APPLICATIONS

This application is a U.S. National Stage Application under 35 U.S.C. § 371 of International Patent Application No. PCT/CN2021/081262, filed Mar. 17, 2021, which claims the benefit of priority of U.S. Provisional Patent Application No. 63/014,954 filed Apr. 24, 2020, both of which are incorporated by reference in their entireties. The International Application was published on Oct. 28, 2021, as International Publication No. WO/2021/213089.

1. FIELD

Disclosed herein is a controlled drug release system of photoresponsive nanocarriers. Also provided are methods of making the nanocarriers. Also provided are methods of using the nanocarriers for the treatment of diseases.

2. BACKGROUND

There are many reported photoresponsive nanocarriers that can achieve light-controlled drug release. However, most of them are constructed by polymeric materials and can only be triggered by UV light, which are quite different from our design. Prof. Adah Almutairi reported a UV light degradable polymer, which allowed drug release triggered by light. However, this system needs intravitreal administration for ocular drug delivery. In addition, there is no phototriggered drug release systems available in the market.

The construction of conventional photoresponsive systems is generally complicated due to the integration of photoresponsive groups into the systems (mainly polymers), which require multiple steps to synthesize. The controlled release process is not fast enough because of the stability of polymeric skeleton. Photoresponsive drug delivery systems usually have limitations of poor light penetration and phototoxicity, which limit their translational applications.

3. SUMMARY

To solve these problems, we designed small clathrin-like (three-legged) molecules that can self-assemble into nanoparticles. The synthesis of these molecules is relatively simple and the nanoparticles can be conveniently constructed via one-step self-assembly in water. Furthermore, the release of encapsulated cargos upon light triggering can be rapid, since the assembly of small molecules can be readily dissociated upon the photocleavage of the molecules. For the light penetration issue, we utilized di-cyano group-modified coumarin, a photocleavable group responsive to green light, instead of the traditional UV light-absorbing coumarin. Green light has deeper tissue penetration depth than UV light. As a proof-of-concept study, drug-loaded nanocarriers were triggered to degrade by light and successfully deliver drugs into the posterior segment of the eye. This strategy also eliminated the phototoxicity because green light is less harmful to normal tissues such as retina than the UV or blue light.

Photoresponsive drug delivery systems (PDDS) are validated to be applicable for spatiotemporally controlled drug release. Nevertheless, the poor light penetration and unreliable drug release process remain challenging for biomedical applications. Here, we developed a novel photoresponsive nanocarrier self-assembled from three-legged small molecules. Compared with other photoresponsive drug delivery systems, this nanocarrier can response rapidly to green light irradiation at 505 nm, which has deeper tissue penetration depth and less phototoxicity than the commonly used UV light. Moreover, the distinctive three-legged molecules can spontaneously self-assemble into nanocarriers and encapsulate hydrophobic drugs in aqueous solutions. As a potential application, we encapsulated doxorubicin (DOX) in the nanocarriers and successfully delivered it into the posterior segment of the eye for the treatment of retinoblastoma. This would be the first example of photoresponsive nanoparticles self-assembled from three-legged molecules. To the best of our knowledge, it is also the first example that light triggers drug release in the eye from photoresponsive drug delivery systems administered intravenously.

Provided herein is a drug delivery system comprising: a nanocarrier and a pharmaceutical agent, wherein the nanocarrier comprises a photoresponsive three-legged molecule that is capable of self-assembly into nanoparticles.

Provided herein is a drug delivery system comprising: a nanocarrier and a pharmaceutical agent, wherein the nanocarrier comprises a formula $(X)_3$-TAEA, wherein X is a photoresponsive molecule, which is capable of self-assembly into nanoparticles.

Provided herein is a drug delivery system comprising: a nanocarrier and a pharmaceutical agent, wherein the nanocarrier comprises $(DEAdcCM)_3$-TAEA (DTAEA) having the formula:

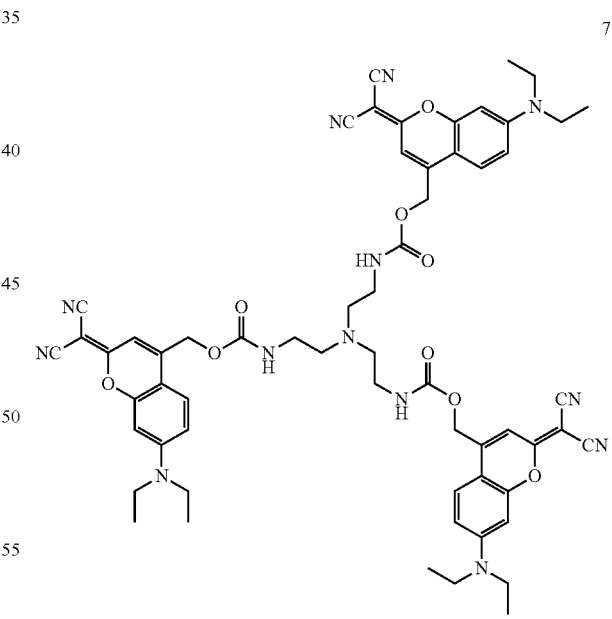

In certain embodiments, the nanocarrier has a size of about 10-300 nm.

In certain embodiments, the nanocarrier has a polydispersity (PDI) of about 0.4 to 0. In certain embodiments, the nanocarrier has a size of about 90 nm with a polydispersity (PDI) of about 0.086.

In certain embodiments, the nanocarrier has a zeta-potential about −10 mV to −40 mV.

In certain embodiments, the nanocarrier has a zeta-potential about −27 mV.

In certain embodiments, the nanocarrier is photoresponsive.

In certain embodiments, the pharmaceutical agent is a hydrophobic drug or imaging dye.

In certain embodiments, the pharmaceutical agent is for imaging or treatment of ocular diseases (like retinoblastoma, age-related macular degeneration, etc.) and other diseases (like melanoma, subcutaneous tumors, esophageal cancer, gastric cancer, etc.) where light can reach its target with a certain way (like using optical fibers).

In certain embodiments, the pharmaceutical agent is doxorubicin (DOX), paclitaxel (PTX), capecitabine, etc.

Provided herein is a method of treating a disease in a subject comprising the steps of: administering the delivery system disclosed herein to the subject and irradiating the subject with a light.

In certain embodiments, the light is delivered by an LED light source, a lamp, a laser source or optical fibers.

In certain embodiments, the nanocarrier is triggered by green light irradiation.

In certain embodiments, the nanocarrier is triggered by blue, red or near-infrared (NIR) irradiation.

In certain embodiments, the light has a wavelength of 600-1200 nm.

In certain embodiments, the light has a wavelength of 400-600 nm.

In certain embodiments, the light is green LED light with a wavelength of 505 nm at 50 mW/cm$^2$ for a duration of 5 mins.

In certain embodiments, the delivery system is administered intravenously.

In certain embodiments, the subject is irradiated 0-4 h after administering the delivery system.

In certain embodiments, the disease is skin carcinoma, esophageal cancer, gastric cancer, eye diseases, retinoblastoma, and other diseases where light can reach its target.

Provided herein is a method of making the system disclosed herein wherein the DTAEA is assembled in the presence of DSPE-mPEG to form the nanocarrier.

Provided herein is a method of synthesizing (DEAdcCM)$_3$-TAEA (DTAEA), said method comprising the steps of:

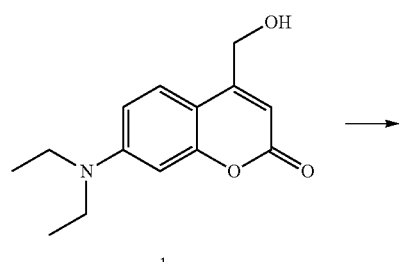

1

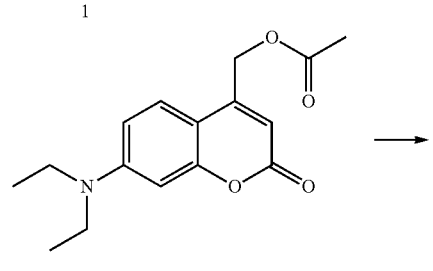

2

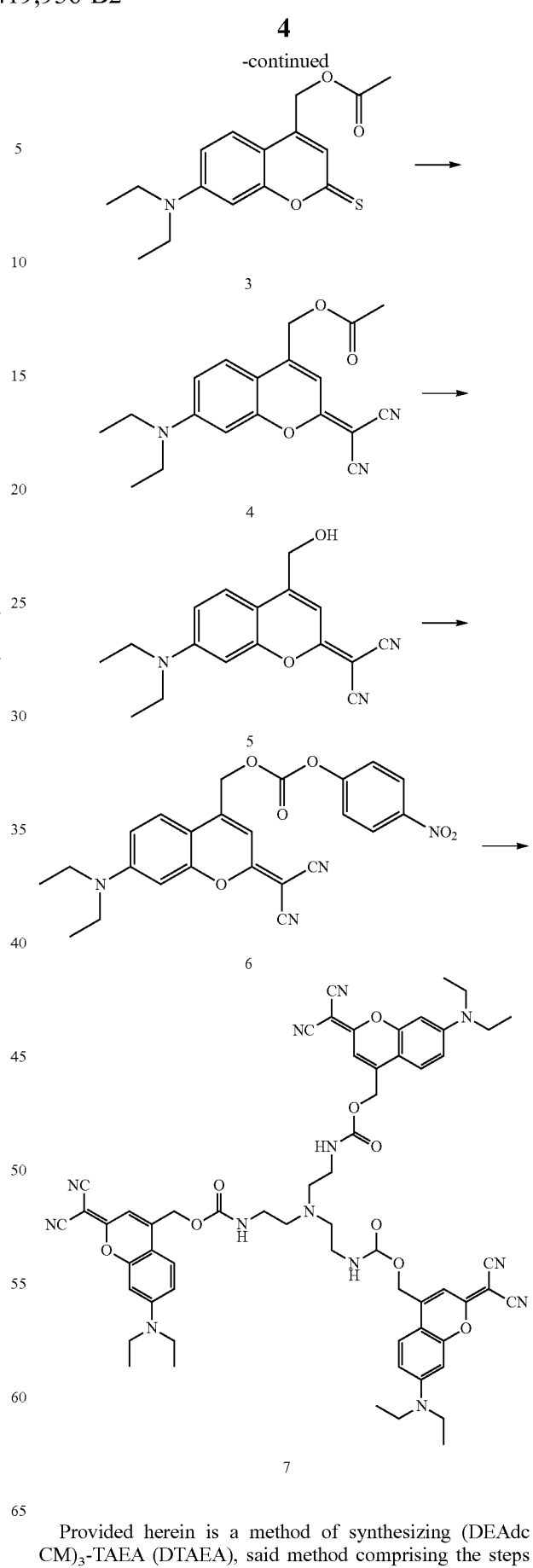

3

4

5

6

7

Provided herein is a method of synthesizing (DEAdcCM)$_3$-TAEA (DTAEA), said method comprising the steps of: (i) modifying 7-(diethylamino)-4-(hydroxymethyl)-coumarin (DEACM) photocage having the structure of

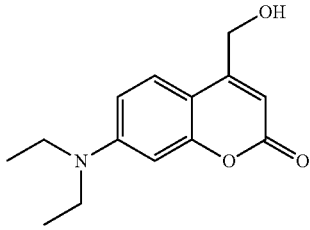

with malononitrile to form dicyanocoumarin (DEAdcCM) having the structure of

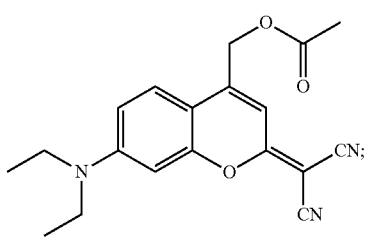

(ii) linking DEAdcCM to TAEA amino groups via a nitrochloroformate-mediated reaction of hydroxyl and amino groups to form DTAEA.

4. BRIEF DESCRIPTION OF DRAWINGS

SCHEME 1—Self-assembly, photodegradation and drug release of Dox-loaded (DEAdcCM)$_3$-TAEA (DTAEA) nanocarrier. The proposed route of drug accumulation in the eye is also presented.

FIG. 1 Synthesis route of DEAdcCM-TAEA (DTAEA).

Figure 2:
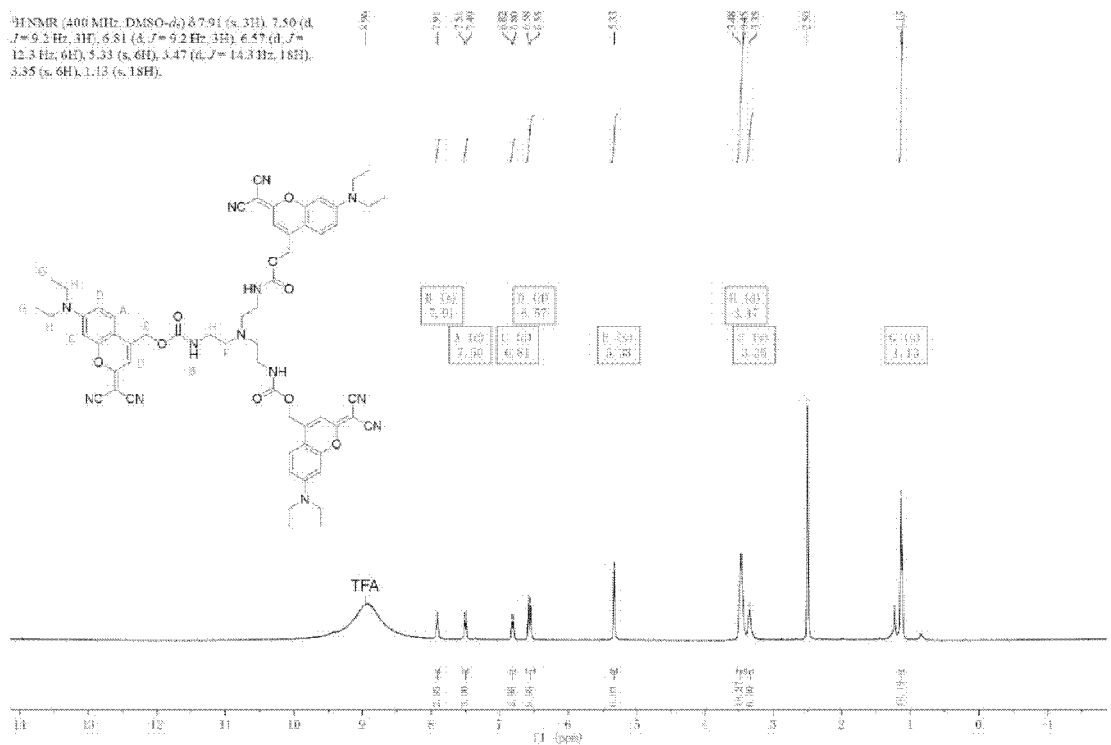

FIG. 2 $^1$H-NMR spectrum of the DTAEA molecule.

Figure 3:
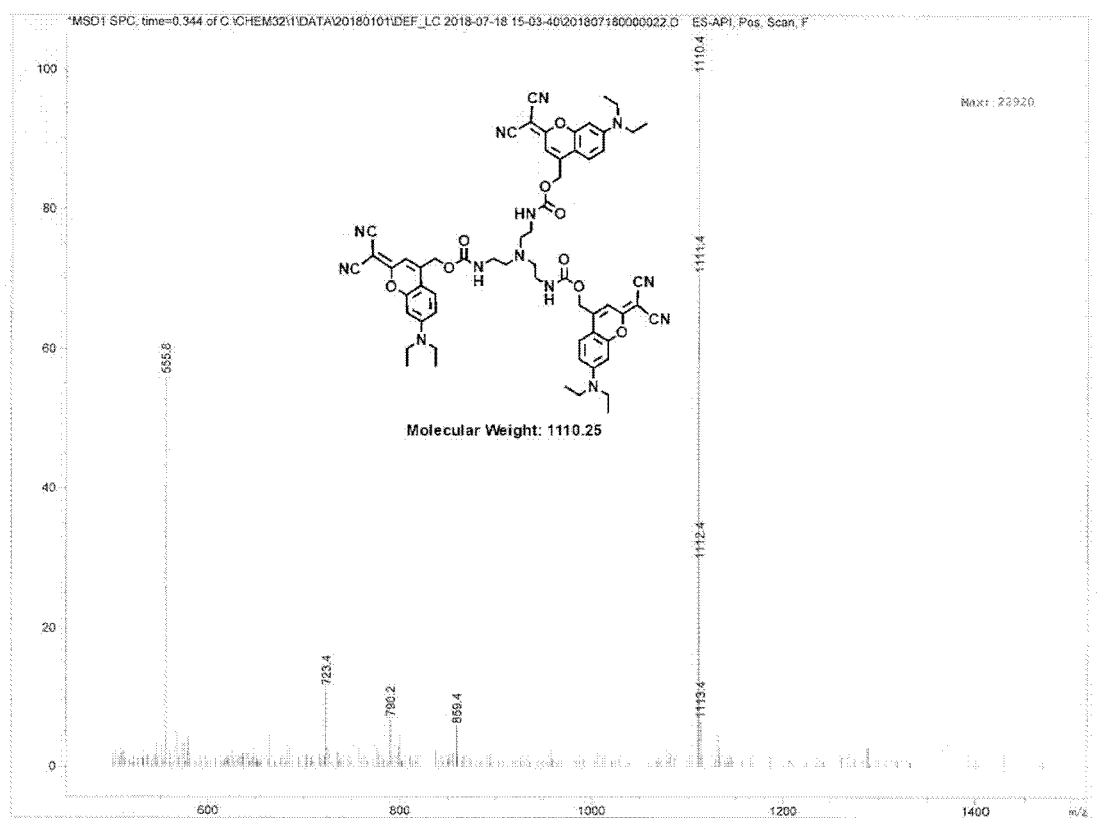

FIG. 3 ESI-MS spectrum of the DTAEA molecule.

Figure 4:
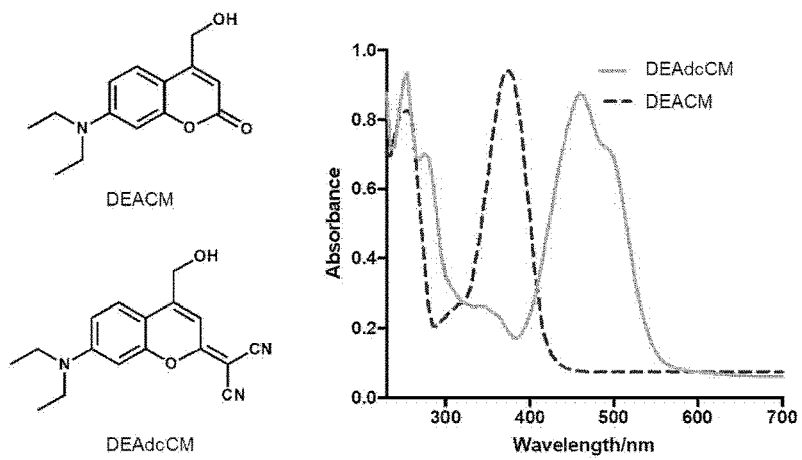

FIG. 4 Structure and UV-vis spectra of two photocleavable groups: coumarin (DEACM) and dicyano-coumarin (DEAdcCM).

Figure 5:
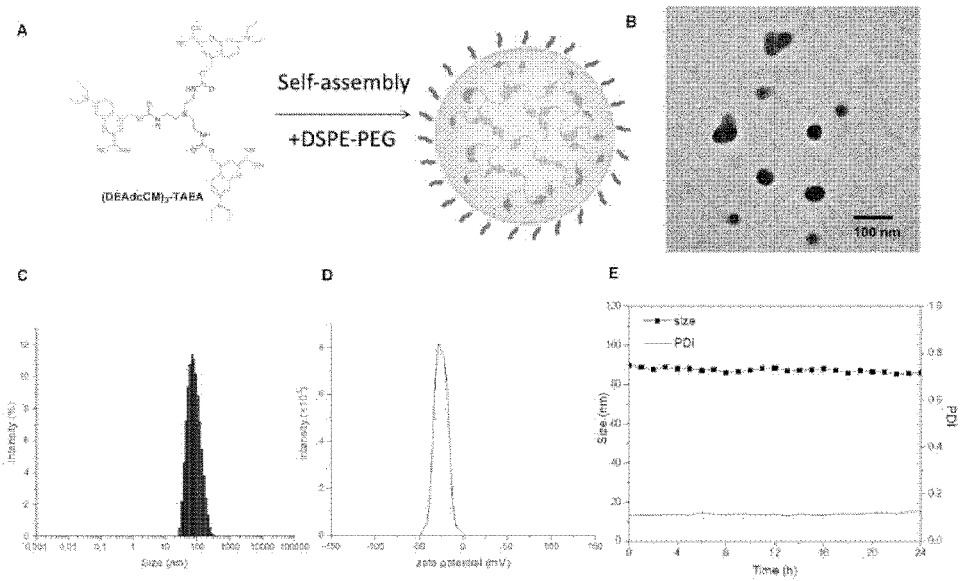

FIG. 5 Self-assembly of DTAEA nanoparticles. (A) Scheme of DTAEA self-assembly. (B) TEM image of DTAEA nanoparticles. (C) Size and (D) zeta potential of DTAEA nanoparticles, peaked at 89.46 nm and −25.1 mV, respectively. (E) The change of size and polydispersity of DTAEA nanoparticles in PBS at 37° C. in 24 h.

Figure 6:
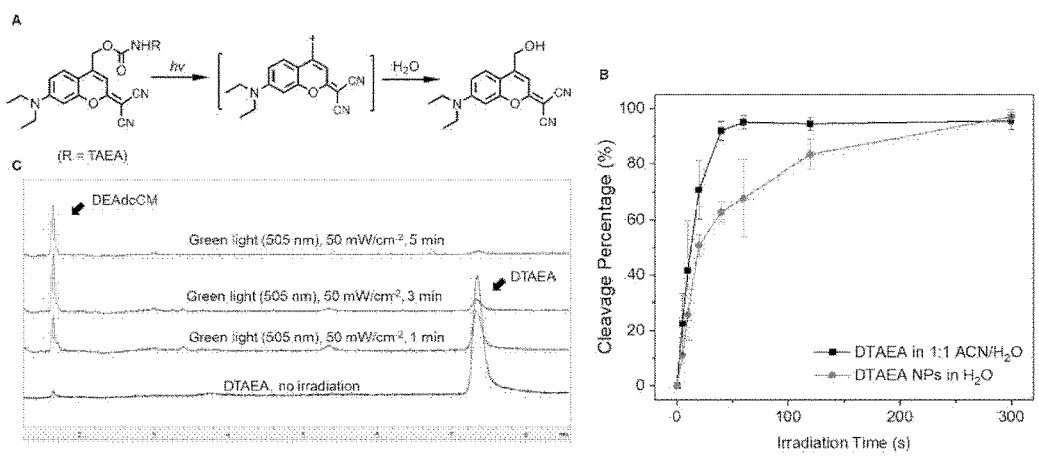

FIG. 6 Photocleavage of DTAEA. (A) Scheme of the proposed photolysis mechanism. (B) Photocleavage rate of DTAEA in 1:1 ACN/H$_2$O (v/v) solution and of DTAEA nanoparticles in water. (C) HPLC curves of DTAEA nanoparticles before and after irradiation in PBS (Mightex LED light source, 505 nm, 50 mW/cm$^2$).

Figure 7:
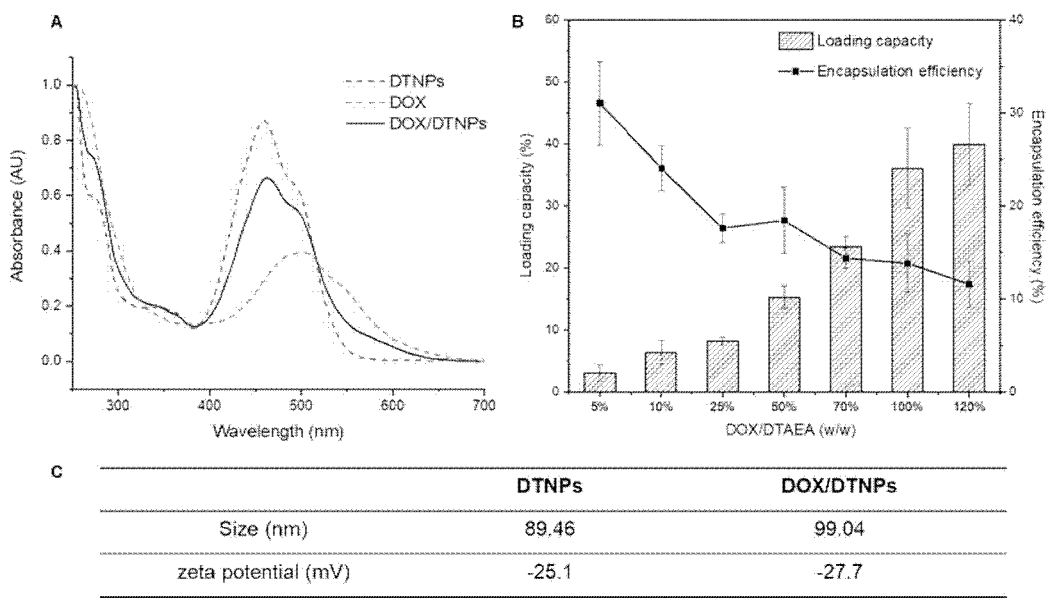

FIG. 7 Characterization of DOX-loaded DTNPs (DOX/DTNPs). (A) UV-vis spectra of DTNPs, DOX/DTNPs and DOX. (B) Encapsulation efficiency and loading capacity of DTNPs with different feeding ratios (DOX/DTAEA, w/w). (C) Size and zeta-potential of DTNPs and DOX/DTNPs.

Figure 8:
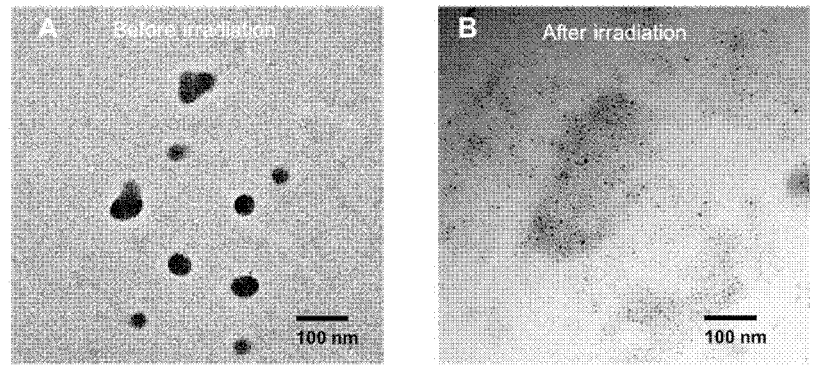

FIG. 8 TEM images of DTNPs before and after light irradiation (505 nm, 50 mW/cm$^2$ for 5 min).

Figure 9:
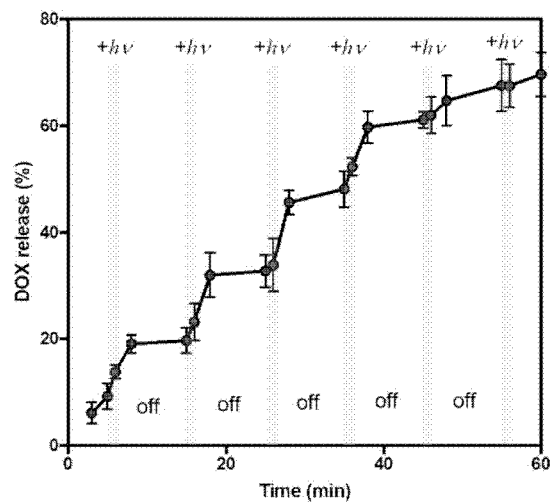

FIG. 9 Light-triggered release profile of DOX from DOX/DTNPs. The nanoparticles were irradiated for 1 min and then dialyzed for 10 min. The released drug molecules were detected by HPLC.

Figure 10:
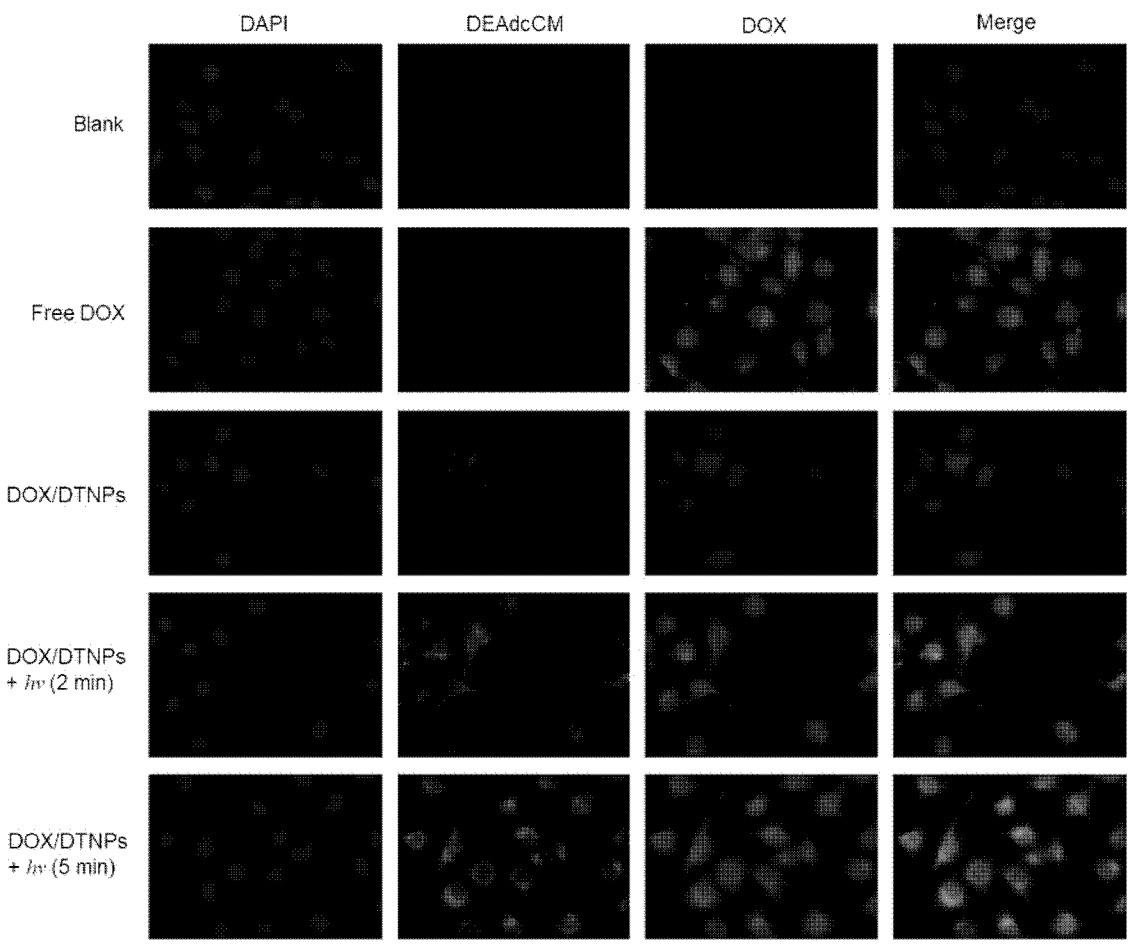

FIG. 10 Light-triggered DOX uptake in HUVEC cells. Representative fluorescent microscopic images of HUVEC cells incubated with various formulations.

Figure 11:
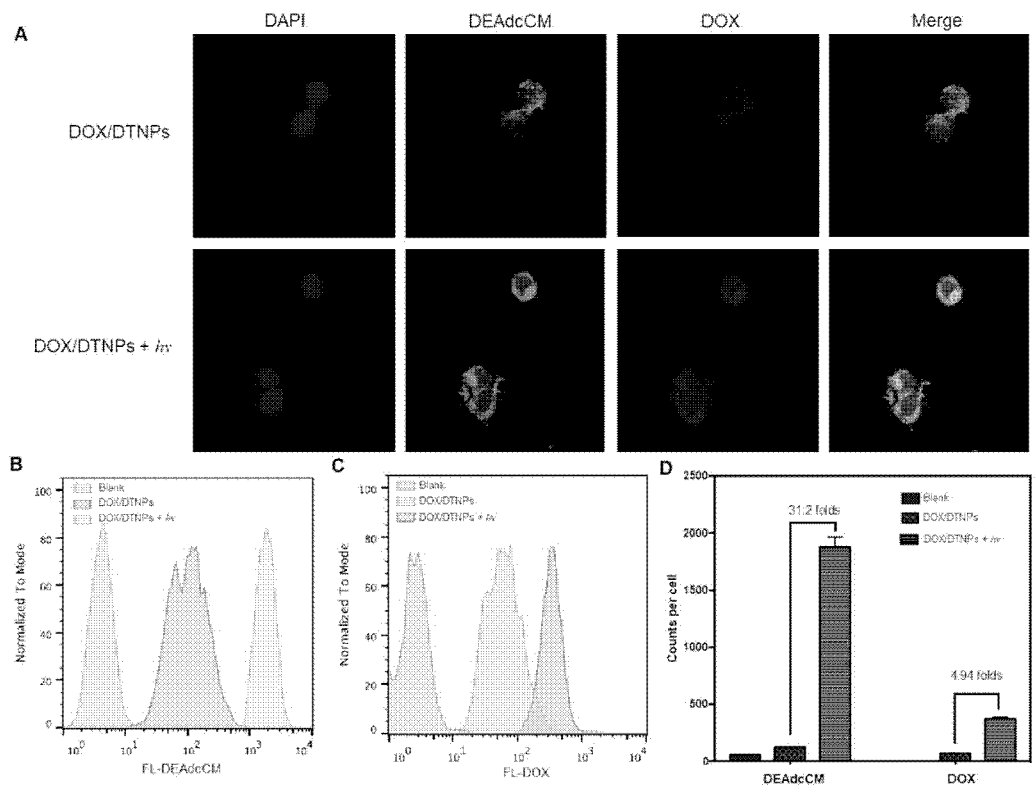

FIG. 11 Light-triggered DOX uptake in WERI-Rb-1 cells. (A) Representative confocal microscopic images of WERI-Rb-1 cells. (B) Representative flow cytometry data of DEAdcCM fluorescence within WERI-Rb-1 cells incubated with DOX/DTNPs and treated with or without irradiation. (C) Representative flow cytometry data of DOX fluorescence within WERI-Rb-1 cells incubated with DOX/DTNPs and treated with or without irradiation. (D) Quantitation of the flow cytometric data (mean of four median values of fluorescence intensity).

Figure 12:
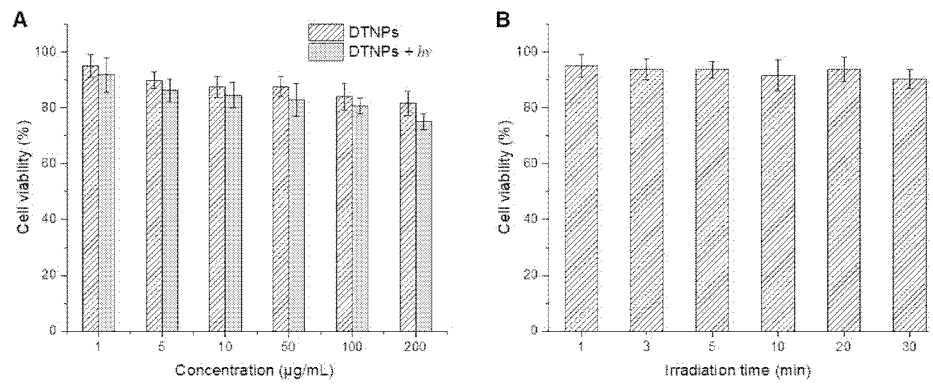

FIG. 12 Cytotoxicity of DTNPs and light irradiation to WERI-Rb-1 cells. (A) Cytotoxicity of DTNPs before and after irradiation (505 nm, 50 mW/cm$^2$, 5 min). (B) Cytotoxicity of the light irradiation (505 nm, 50 mW/cm$^2$) for various time periods.

Figure 13:
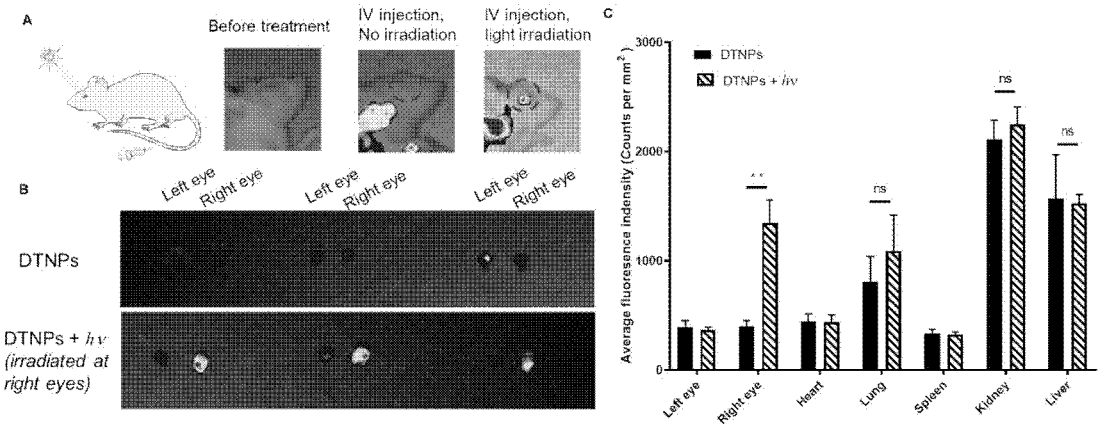

FIG. 13 Light-controlled DOX release from DOX/DTNPs in retinoblastoma-bearing mice. (A) Representative IVIS fluorescent images of the mice 1 h after the injection of DTNPs. (B) Representative fluorescent images of the mouse eyes 1 h after the injection of DOX/DTNPs. (C) Fluorescence intensity of different tissues of the mice 1 h after the injection of DOX/DTNPs. The light irradiation (505 nm, 50 mW/cm$^2$, 5 min) was performed at the right eyes immediately after injection.

Figure 14:
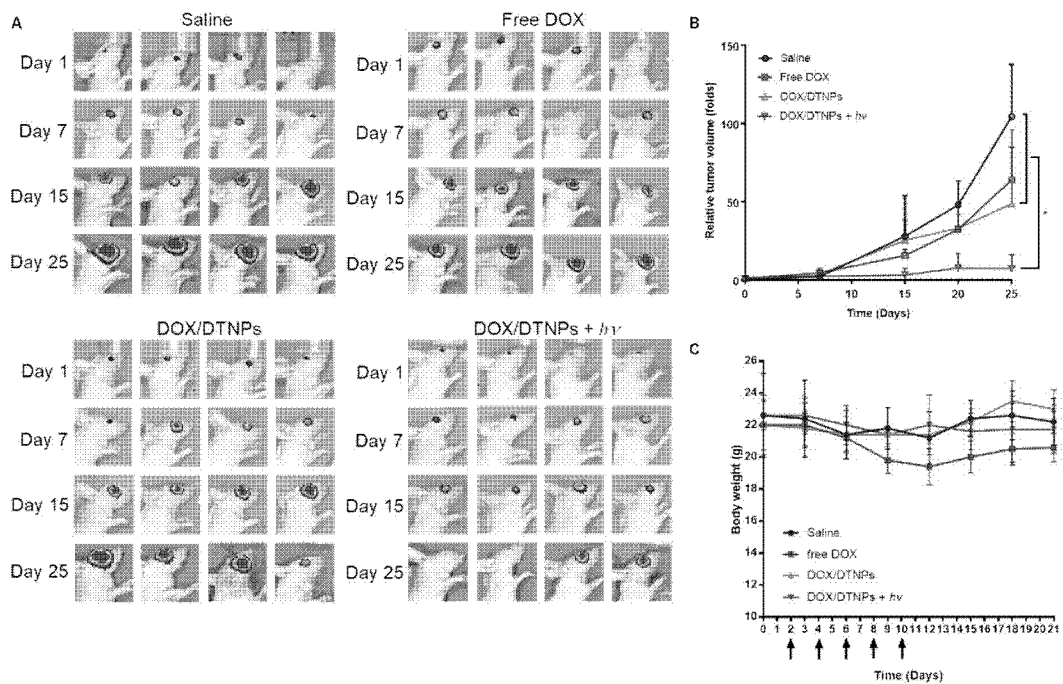

FIG. 14 Intravenous injection of formulations for chemotherapy in orthotopic WERI-Rb GFP-luc tumor-bearing BALB/c nude mice. For the irradiation group, the formulations were intravenously injected and then irradiated at the right eyes of the mice (505 nm, 50 mW/cm$^2$, 5 min). (A) In vivo bioluminescence images of the eyes. Pictures were captured and analyzed using Live Imaging 4.5.2 software. For each group, the images were shown at day 1, 7, 15, and 25 after treatments. (B) Tumor growth curve in each group. The data were shown as means±SD (n=4). *p<0.05. (C) Body weight changes (n=4).

Figure 15:
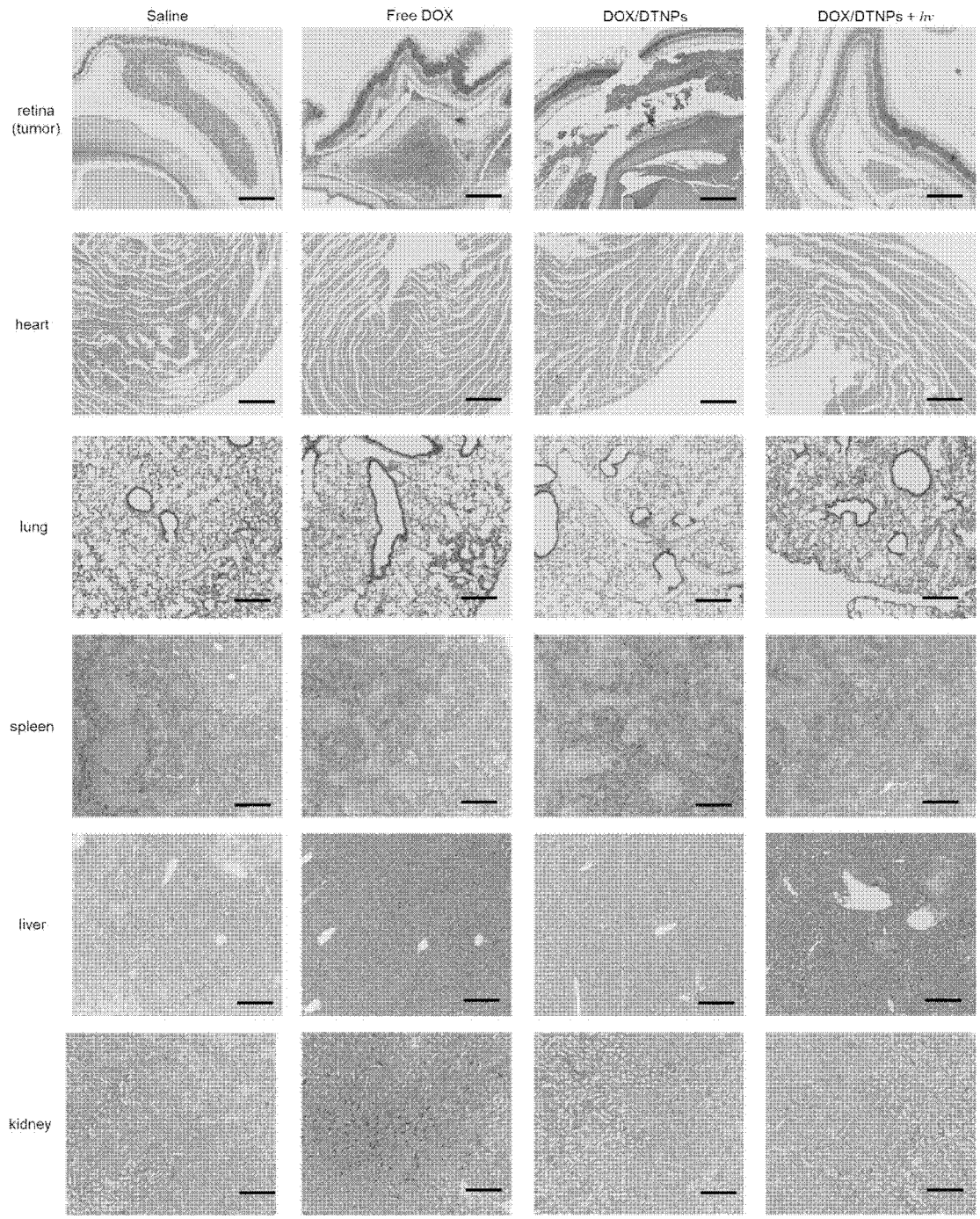

FIG. 15 Representative photomicrographs of hematoxylin & eosin-stained sections of retina (with tumor), heart, lung, spleen, liver and kidney from four groups (saline, free doxorubicin, DOX/DTNPs, and DOX/DTNPs+irradiation). The scale bar is 50 μm.

Figure 16:
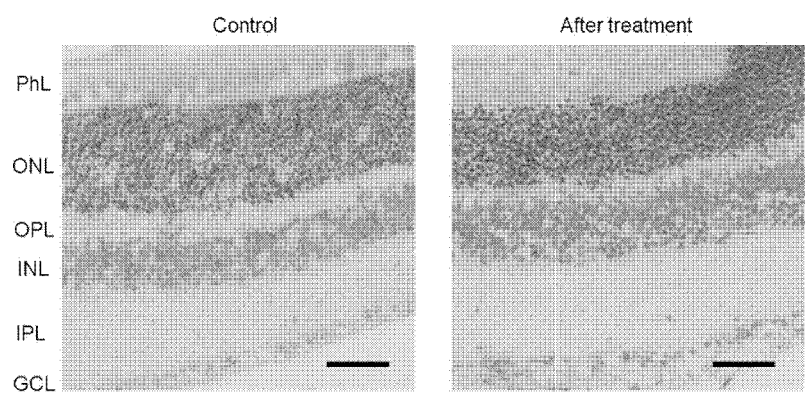

FIG. 16 Representative photomicrographs of hematoxylin & eosin-stained sections of retina of the control group and the group treated with DOX/DTNPs and light irradiation (505 nm, 50 mW/cm$^2$, 5 min×5 in 10 days). PhL, photoreceptor layer; ONL, outer nuclear layer; OPL, outer plexiform layer; INL, inner nuclear layer; IPL, inner plexiform layer; GCL, ganglion cell layer. The scale bar is 10 μm.

5. DETAILED DESCRIPTION

Photoresponsive drug delivery systems (PDDS) can spatiotemporally control drug release, which are promising for biomedical applications.[1,2] Nevertheless, the unreliable drug release process and poor light penetration depth in biological tissues remain challenging for the further development of the systems.[3] Here, we developed a novel photocleavable three-legged small molecule (Scheme 1), which can self-assemble into nanocarriers to encapsulate hydrophobic drugs.[4,5] As the three-legged small molecules are the main building blocks of the nanocarriers, the cleavage of the three-legged molecules upon light irradiation can quickly lead to the breakdown of the nanocarriers, resulting in the rapid release of the drugs only at the irradiated sites. Moreover, compared with conventional photoresponsive drug delivery systems, this nanocarrier system can be triggered by green light irradiation, which has deeper tissue penetration depth and lower phototoxicity than the commonly used UV light.[6] To demonstrate the potential application of the system, the anticancer drug doxorubicin (DOX) was encapsulated into the nanocarriers for the treatment of retinoblastoma (Scheme 1). A 505 nm LED was used to trigger the release of DOX to kill cancer cells at the posterior segment of the eye. It should be noted that the nanocarriers can be intravenously administrated for the treatment, which can reduce the suffering and side effects of the conventional intravitreal injection. The green light penetrates deep enough for treating superficial diseases such as skin carcinoma and eye diseases. This is the first demonstration that light triggers drug release for the treatment of retinoblastoma with intravenous administration.

6. EXAMPLES

Synthesis and Self-Assembly of DTAEA Molecules

The photoresponsive three-legged molecule, (DEAdcCM)$_3$-TAEA (DTAEA), was synthesized by coupling the dicyanocoumarin (DEAdcCM) with the three amine groups of tris(2-aminoethyl) amine (TAEA). FIG. 1 shows the synthesis route, the detail of which are provided in the Experimental Section. In brief, the commercially available 7-(diethylamino)-4-(hydroxymethyl)-coumarin (DEACM) photocage (compound 1) was modified with malononitrile to give dicyanocoumarin (DEAdcCM) (compound 4) as an intermediate. DEAdcCM was then linked to the amino groups of TAEA via a nitrochloroformate-mediated reaction of hydroxyl and amino groups. After purification by column chromatography, the $^1$H nuclear magnetic resonance ($^1$H NMR) (FIG. 2) and electrospray ionization-mass spectrometry (ESI-MS) (FIG. 3) spectra of the product confirmed the successful synthesis of DTAEA molecules. DEAdcCM showed a broad UV-vis absorption with two peaks at 480 nm and 505 nm, separately. Compared to the UV-light-responsive DEACM photocage (absorption peaked at 380 nm), DEAdcCM has a red-shifted absorption of visible light in the blue-green light range (FIG. 4), which would be more favorable for biomedical applications.

The photoresponsive nanocarriers were constructed via nanoprecipitation method. DTAEA can readily self-assemble into nanoparticles in aqueous solutions. It is proposed that the π-π stacking interaction between DEAdcCM groups can facilitate the self-assembling process.[4,5] During the self-assembling process, DSPE-mPEG$_{2000}$ can co-assemble with DTAEA for surface PEGylation (FIG. 5a). Dynamic light scattering (DLS) analysis showed the size of PEGylated DTAEA nanoparticles (abbreviated as DTNPs) was around 90 nm with a narrow polydispersity (PDI) of 0.086 (FIG. 5c). Morphology of DTNPs under transmission electron microscopy (TEM) showed well-dispersed nanoparticles with the diameter of 70-100 nm (FIG. 5b). Moreover, the zeta-potential of DTNPs was around −27.0 mV (FIG. 5d), which would stabilize the nanoparticles and avoid aggregation, due to the electrostatic repulsion between negatively charged DTNPs.[8] To confirm the water stability, size and PDI of DTNPs were monitored in PBS for a duration of time. After incubated at 37° C. for 24 hours, DTNPs remained stable and had no obvious change of the size and PDI in PBS (FIG. 5e).

Photocleavage and In Vitro Drug Release

The photocleavage mechanism of coumarin carbamate derivatives was reported as carbocation formation following with the addition of —OH group in aqueous solutions (FIG. 6a).[9] To quantitatively measure the photocleavage rate of free DTAEA, quartz cuvettes containing DTAEA in 50% acetonitrile/H$_2$O was irradiated with 505 nm green LED light. At predetermined time points, the remaining DTAEA and released DEAdcCM were determined by high performance liquid chromatography (HPLC). More than 90% of DTAEA were cleaved under the irradiation (505 nm, 50 mW/cm$^2$) for 1 min (FIG. 6b), revealing the rapid photoresponsive process of DTAEA. The similar photocleavage process in DTAEA NPs took about 5 minutes for the completely consumption of DTAEA (FIG. 6c), which was slightly slow down compared to free DTAEA in the mixture of acetonitrile and water. The hydrophobic environment of the nanoparticles which retarded the nucleophilic attack of carbocation intermediate by water molecules may be responsible for this result. Based on the photocleavage performance of DTAEA and DTNPs, the irradiation duration was set to be no less than 5 min with 505 nm green LED light at 50 mW/cm$^2$.

Doxorubicin (DOX) has showed outstanding anticancer efficacy for the treatment of retinoblastoma.[10] Herein, we chose DOX as the cargo to be encapsulated into the DTNPs. UV-vis spectrum of the DOX-loaded DTNPs (DOX/DTNPs) showed broad absorption from 400 nm to 650 nm (FIG. 7a), which covered the absorption regions of DTAEA and DOX, demonstrating the successful encapsulation of DOX in DTNPs. Then, loading capacity and encapsulation efficiency were optimized by feeding different ratios of DOX to DTAEA during flash nanoprecipitation (FIG. 7b). With the increase of the DOX-to-DTAEA ratio, the loading capacity of DOX increased from 3.0% (1:20 DOX/DTAEA, w/w) to 36.0% (1:1 DOX/DTAEA, w/w). Further increasing DOX content resulted in bulk aggregation and significant decrease of encapsulation efficiency, so we chose 1:1 DOX-to-DTAEA ratio for the preparation of DOX/DTNPs in the following study. The encapsulation efficiency of DOX at this ratio was calculated to be 13.6%. Moreover, the size and zeta potential of DOX/DTNPs did not change much compared to the cargo-free DTNPs (FIG. 7c), which implied that the drug loading would not influent the stability and surface properties of DTNPs.

The photo-induced breakdown of nanocarriers was investigated by comparing the TEM images of DTNPs before and after light irradiation. As shown in FIG. 8, after exposure to green light (505 nm, 50 mW/cm$^2$) for 5 min, DTNPs were disassociated into smaller fragments and no nanoparticles at original size was observed. This light-triggered degradation of nanoparticles could lead to a burst release of drugs. To further evaluate the photo-triggered drug release performance, the aqueous solution of DOX/DTNPs was discontinuously irradiated by 505 nm light at intervals of 10 min. After each irradiation for 1 min, the solution was dialyzed against deionized water to separate the released drugs for quantitative determination by HPLC. As shown in FIG. 9, the light-triggered release of doxorubicin exhibited a ON—OFF pattern upon irradiation at intervals. The released DOX can achieve to ~60% of the encapsulated DOX after the irradiation for 5 times. This result revealed that the dissociation of DTNPs and DOX release can be precisely controlled by green light LED with a low-irradiance at 50 mW/cm$^2$.

Light-Triggered Cellular Uptake of Drugs

We further investigated the cellular uptake of the photo-released DOX by fluorescence microscopy and flow cytometry. In this work, human umbilical vein endothelial cells (HUVEC) and human retinoblastoma cells (WERI-Rb-1) were employed to investigate the cellular uptake. The cells were treated with various formulations, including free DOX, DOX/DTNPs and DOX/DTNPs+light irradiation (hv). As shown in FIG. 10 and FIG. 11a, the cells treated with DOX/DTNPs and green light irradiation showed stronger fluorescent intensities both in the green channel (DEAdcCM) and red channel (DOX) compared to those cells without irradiation, demonstrating the increased cellular uptake of both DEAdcCM and DOX upon light irradiation. Furthermore, in FIG. 10, the red florescence intensity in the free-DOX-incubated cells was as high as the irradiated group, both of which were much higher than the non-irradiation group. It is worthwhile to mention that the DOX fluorescence was observed in the cell nuclei both in the free DOX group and the irradiated group, while the DOX/DTNPs without irradiation only exhibited cytoplasm distribution, indicating DOX did not release from the DOX/DTNPs without irradiation.

Flow cytometry was utilized to quantitatively investigate the cellular uptake of DEAdcCM and released DOX. (FIG. 11 b, c, d) The WERI-Rb-1 cells treated with DOX/DTNPs+hv showed 4-fold higher DOX fluorescence intensity and 31.2-fold higher DEAdcCM fluorescence intensity than that of non-irradiation cells, which showed the same trend with fluorescence microscopy results. Besides, the increased fluorescence intensity of DOX and DEAdcCM can be served as an obvious signal for drug release monitoring and tumor imaging. Moreover, the cytotoxicity of DTNPs and the phototoxicity of the green light irradiation against WERI-Rb-1 cells were investigated by cell prohibition study via the MTT assay. We found no obvious cytotoxicity of cargo-free DTNPs in the concentration ranging from 1 to 200 µg/mL with or without irradiation (FIG. 12a). The green-light irradiation at 505 nm and 50 mW/cm$^2$ is also harmless to the cells even for up to 30 min (FIG. 12b).

All these results demonstrated that the green light can trigger DOX release from DOX/DTNPs, which increases the cellular uptake of the drugs. Besides, the drug release process is monitorable based on the fluorescence of DEAdcCM and doxorubicin from incubated cells. DOX/DTNPs is useful for the application in in vivo targeted drug delivery with local irradiation at the diseased site.

Light-Triggered Intraocular Drug Accumulation

To validate that DOX/DTNPs can achieve light-controlled drug delivery in vivo, orthotopic retinoblastoma tumor model was established to evaluate the biodistribution and therapeutic effect. Generally, WERI-Rb-1 cells were injected slowly into the vitreous cavity at the right eyes of Bulb/c nude mice for the tumor implantation. The tumor-bearing mice were further fed for one week and then intravenously injected with DOX/DTNPs and then treated with or without irradiation. The light irradiation was performed at the right eyes immediately after injection. The combined fluorescence of DEAdcCM and doxorubicin from DOX/DTNPs can be observed in the right eyes (FIG. 13a) once the irradiation was performed after the I.V. injection, while minimum fluorescent signal was found in the non-irradiated left eyes of the irradiated group and in the both sides of eyes of the non-irradiated group.

To evaluate the biodistribution, the mice were euthanized after the above treatment, and their eyes (both sides), heart, lung, liver, spleen and kidney were further exteriorized for ex vivo fluorescence imaging. Higher fluorescence intensity was observed in the right eyes of the irradiated group (FIG. 13b) compared to the others (both sides of eyes of non-triggered group and left eyes of triggered group). No significant difference in heart, lung, liver, spleen or kidney between groups with and without irradiation (FIG. 13c), revealing that the localized ocular illumination cannot trigger drug release in other organs but only in the irradiated eyes. This finding confirmed that we successfully delivered drugs into orthotopic tumor-bearing eyes by the light-controlled release of DOX from DTNPs. The photocleavage process was fast enough to achieve burst drug release at the irradiated sites and resulted in localized drug accumulation. Moreover, the non-specific side effects of conventional chemotherapy would be almost eliminated because the light irradiation did not trigger drug accumulation in other organs excepted for the irradiated eyes.

Therapeutic Effect of Photoresponsive DOX/DTNPs on Retinoblastoma

To evaluate the in vivo therapeutic effect, WERI-Rb-1 cells were transfected with green fluorescent protein (GFP) and luciferase genes (abbreviated as WERI-Rb-1-GFP-luc) for in vivo tumor size monitoring. Seven days after the intraocular injection of WERI-Rb-1-GFP-luc cells, the luminescence signals from the cells can be determined by in vivo imaging system for in situ monitoring of orthotopic ocular tumors. The WERI-Rb-1-GFP-luc orthotopic tumor-bearing mice were randomly divided into 4 groups and intravenously treated with normal saline, free DOX, DOX/DTNPs and DOX/DTNPs+hv. The dosage of drug administration was precisely controlled based on the body weight of mice and set as 5 mg/kg body weight. The I.V. injection of formulations was applied every two days for five times. For the group of DOX/DTNPs+hv, after each I.V. injection of the formulations, the green LED light (505 nm, 50 mW/cm$^2$) was utilized to perform irradiation at the right eyes for 5 min. During the treatment, bioluminescence from the tumors was detected for tumor growth monitoring. As shown in FIG. 14a, the eyes treated with DOX/DTNPs and the green-light irradiation showed a much slower increase of tumor bioluminescence intensity than those treated with other formulations (saline, free DOX, DOX/DTNPs without irradiation). Considering individual differences, tumor growth curves (FIG. 14b) of different groups were obtained by setting the bioluminescence intensity on the day before treatment (Day 0) as the origin and determining the quantitative changes in the subsequent days. On the Day 15, the group of DOX/DTNPs+hv began to show significant effect in tumor inhibition over other formulations. On the Day 25, the increase of bioluminescence intensity in eyes treated with DOX/DTNPs+hv (7.3 folds, compared to Day 0) was significantly lower than those in the groups of saline (104.5 folds, compared to Day 0), free DOX (64.0 folds, compared to Day 0) and DOX/DTNPs (48.7 folds, compared to Day 0). It should be noted that two of the mice treated with DOX/DTNPs+hv showed no bioluminescence signal on the Day 25, indicating that their tumors were completely eliminated. Moreover, the body weight (FIG. 14c) of the free DOX-treated mice decreased about 10% during the drug administration period (Day 0 to Day 10), due to the serious side effect of the chemotherapeutic drug. In the group treated with DOX/DTNPs, no obvious body weight loss was observed during the treatment, indicating unnoticeable systemic toxicity at least for 25 days. The histological patterns of tumor-bearing retina and main organs were studied by hematoxylin and eosin (H&E) staining (FIG. 15 and FIG. 16). Compared to the healthy retina, there was no histological alteration in the retina after receiving the treatment (DOX/DTNPs+hv) for 25 days, indicating the DOX/DTNPs and green light irradiation were safe to the retina under the therapeutic regimen. Apart from the retina, main organs exhibited no apparent necrosis at the end of the treatment, indicating low systemic toxicity of the intravenously injected DOX/DTNPs with irradiation at diseased eyes. Therefore, intravenous injection of DOX/DTNPs with irradiation at the diseased eye achieved both high therapeutic efficacy for retinoblastoma and low systemic toxicity. The low systemic toxicity of DOX/DTNPs with irradiation compared with free DOX is reasonably attributed to the prolonged circulation time of PEGylated nanoparticles and less absorption in liver and spleen. The rapid DOX release triggered by low irradiance green LED light facilitated drug accumulation in the posterior segment of the eye, where the drug can take its effect for the retinoblastoma treatment.

In summary, we developed a photocleavable three-legged molecule DTAEA, which can self-assemble into light-responsive nanocarriers. As an example, a hydrophobic drug DOX was encapsulated into the nanocarrier to achieve light-controlled drug delivery. Light irradiation triggered DOX release in orthotopic retinoblastoma-bearing mice and achieved good anticancer efficacy. Besides ocular diseases, this light-responsive drug delivery system can be applied for other diseases, where light can reach the diseased sites.

Synthesis of (DEAdcCM)$_3$-TAEA Three-Legged Molecule:

Compound 2: 7-Diethylamino-4-hydroxymethylcoumarin (DEACM, compound 1) (300 mg, 1.2 mmol) was dissolved in dry dichloromethane (DCM) (20 mL) in a duplex flask. Then acetic acid (83 µL, 1.44 mmol, 1.2 eq) and 4-(dimethylamino) pyridine (DMAP) (180 mg, 1.44 mmol, 1.2 eq) was added into the solution of DEACM. The mixture was cooled to 0° C. and protected with nitrogen gas. 1,3-Dicyclohexylcarbodiimide (300 mg, 1.44 mmol, 1.2 eq) was added slowly into the former solution. After stirring for 10 minutes at 0° C., the mixture was warmed up to room temperature and stirred for 12 hours in the dark. The mixture was then ten-fold diluted by DCM and washed with 1.2 M hydrochloric acid and saturated aqueous sodium hydrogen carbonate for three times separately. The organic layer was collected and dried over sodium sulfate and concentrated under vacuum. The residue was purified on chromatography column by using 20:1 DCM/MeOH (v/v) to give compound 2 as the yellow powder (Yield: 311 mg, 88.6%).

Compound 3: Compound 2 (311 mg, 1.1 mmol) and Lawesson's reagent (285 mg, 0.68 mmol, 0.62 eq) were dissolved in dry toluene (40 mL) and protected by nitrogen gas in the dark. The mixture was heated to 115° C. and refluxed for 12 hours. The solvent was removed by rotary evaporation and the residue was loaded into silica column directly. The product was eluted by dichloromethane to give orange yellow powder as the product (Yield: 220 mg, 77.6%).

Compound 4: Compound 3 (175 mg, 0.57 mmol) and malononitrile (52 mg, 0.91 mmol) were dissolved in 4 mL acetonitrile (ACN). The mixture was added into triethylamine (0.3 mL) and stirred for 2 hours in the dark at room temperature. Thin layer chromatography was used to confirm the complete consumption of compound 2. Then AgNO$_3$ (221.8 mg, 1.3 mmol) was added and stirred for 2 hours. After filtration, the solvent was removed by rotary evaporation. The residue was purified on chromatography column by using 1:1 Hexene/DCM (v/v) to give compound 4 as the orange red powder (Yield: 140 mg, 72.4%).

Compound 5: Compound 4 (140 mg, 0.41 mmol) was dissolved in absolute ethanol (50 mL) and aqueous HCl (37%, 33.6 mL, 0.4 mol) was added slowly. The resulting mixture was refluxed at 85° C. for 16 hours in the dark under nitrogen gas. The solvent was removed under reduced pressure and purified on chromatography column by using DCM to give compound 5 as the orange powder (Yield: 108 mg, 88.2%).

Compound 6: Compound 5 (108 mg, 0.37 mmol) was dissolved in 10 mL dry DCM. N,N-Diisopropylethylamine (DIPEA, 0.71 mL, 4.1 mmol) was added and the mixture was cooled to 0° C. in the dark. After stirred for 15 minutes, the solution of 4-nitrophenyl chloroformate (0.83 g, 4.1 mmol) in 5 mL dry DCM was dropwise added into the above solution. The resulting mixture was allowed to warm to room temperature and stirred for 6 hours. The mixture was washed by 0.01 M aqueous HCl solution (100 mL×2). The organic layer was collected and evaporated under reduced pressure. The residue was purified on chromatography column by using 20:1 DCM/ethyl acetate (v/v) to give compound 6 as the red powder (Yield: 153 mg, 90.8%).

Compound 7 (DTAEA): Compound 6 (153 mg, 0.33 mmol) was dissolved in 1.5 mL dry DCM under nitrogen gas and cooled to 0° C. DIPEA (105 µL, 0.6 mmol) was added and stirred for 15 minutes. The solution of tris(2-amino-ethyl) amine (TAEA, 15 µL, 0.1 mmol) in 1 mL dry DCM was slowly added into the former solution at 0° C. The resulting mixture was allowed to warm to room temperature. After stirred for about 1 hour, a small amount of precipitation can be observed. Then, more DIPEA (105 µL, 0.6 mmol) was added and the mixture was stirred overnight. Thin layer chromatography was used to confirm the complete consumption of compound 6. Then the residue was evaporated under reduced pressure and loaded on the chromatography column. DCM/MeOH (0% to 4%) was used to elute the final product as the orange powder (Yield: 78 mg, 63.4%).

REFERENCE

[1] Yafei Li, Yaming Zhang, and Weiping Wang, *Nano Research*, 2018, 11 (10), 5424-5438.

[2] Yanfei Wang, Chi-Hsiu Liu, Tianjiao Ji, Manisha Mehta, Weiping Wang, Elizabeth Marino, Jing Chen and Daniel S. Kohane, *Nature Comm.*, 2019, 10, 804.

[3] S. Stolik, J. A. Delgado, A. Perez and L. Anasagasti, *Journal of Photochemistry and Photobiology B: Biology*, 2000, 57 90-93.

[4] Weiping Wang and Ying Chau, *Chem. Commun.*, 2011, 47 (37), 10224-10226.

[5] Weiping Wang and Ying Chau, *Chem. Mater.*, 2012, 24 (5), 946-953.

[6] Alina Y. Rwei, Weiping Wang, and Daniel S. Kohane, *Nano Today*, 2015, 10 (4), 451-467.

[7] Shields Carol, Lally Sara, Leahey Ann, Jabbour Pascal, Caywood Emi, Schwendeman Rachela and Shields Jerry, *Current Opinion in Ophthalmology*, 2014, 25 (5), 374-385.

[8] Albert Gandioso, Marta Palau, Alba Nin-Hill, Ivanna Melnyk, Carme Rovira, Santi Nonell, Dolores Velasco, Jaume Garcia Amorós and Vicente Marchan, *ChemistryOpen*, 2017, 6, 375-384.

[9] Ji-Young Kim, Jin-Ki Kim, Jeong-Sook Park, Youngro Byun and Chong-Kook Kim, *Biomaterials*, 2009, 30, 5751-5756.

[10] Ruijuan Gao, Rajendra Narayan Mitra, Min Zheng, Kai Wang, Jesse Christine Dahringer, and Zongchao Han, *Adv. Funct. Mater.* 2018, 28, 1806248.

The foregoing description of the specific embodiments will so fully reveal the general nature of the disclosure that others can, by applying knowledge within the skill of the relevant art(s) (including the contents of the documents cited and incorporated by reference herein), readily modify and/or adapt for various applications such specific embodiments, without undue experimentation, without departing from the general concept of the present disclosure. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present disclosure have been described above, it should be understood that they have been presented by way of examples, and not limitation. It would be apparent to one skilled in the relevant art(s) that various changes in form and detail could be made therein without departing from the spirit and scope of the disclosure. Thus, the present disclosure should not be limited by any of the above-described exemplary embodiments but should be defined only in accordance with the following claims and their equivalents.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A drug delivery system comprising: a nanocarrier and a pharmaceutical agent, wherein the nanocarrier comprises (DEAdcCM)$_3$-TAEA (DTAEA) having the formula:

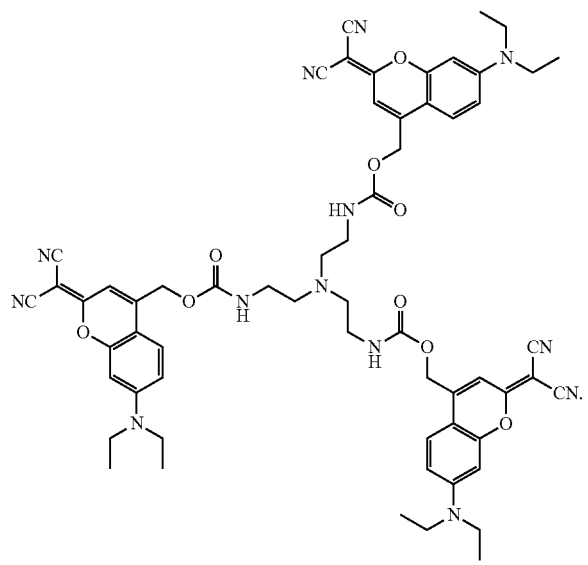

2. The system of claim 1 wherein the nanocarrier has a size of about 10-300 nm.

3. The system of claim 1 wherein the nanocarrier has a polydispersity (PDI) of about 0.4 to 0.

4. The system of any one claim 1 wherein the nanocarrier has a size of about 90 nm with a polydispersity (PDI) of about 0.086.

5. The system of any one of claim 1 wherein the nanocarrier has a zeta-potential about −10 mV to −40 mV.

6. The system of claim 1 wherein the nanocarrier has a zeta-potential about −27 mV.

7. The system of claim 1 wherein the nanocarrier is photoresponsive.

8. The system of claim 1 wherein the pharmaceutical agent is a hydrophobic drug or imaging dye.

9. The system of claim 1 wherein the pharmaceutical agent is for imaging or treatment of retinoblastoma, age-related macular degeneration, melanoma, subcutaneous tumors, esophageal cancer, or gastric cancer.

10. The system of claim 1 wherein the pharmaceutical agent is doxorubicin (DOX), paclitaxel (PTX), or capecitabine.

11. A method of treating a disease in a subject comprising the steps of:
    administering the delivery system of claim 1 to the subject and irradiating the subject with a light.

12. The method of claim 11 wherein the light is delivered by an LED light source, a lamp, a laser source or optical fibers.

13. The method of claim 11 wherein the nanocarrier is triggered by green light irradiation.

14. The method of claim 11 wherein the nanocarrier is triggered by blue, red or near-infrared (NIR) irradiation.

15. The method of claim 11 wherein the light has a wavelength of 600-1200 nm.

16. The method of claim 11 wherein the light has a wavelength of 400-600 nm.

17. The method of claim 11 wherein the light is green LED light with a wavelength of 505 nm at 50 mW/cm$^2$ for a duration of 5 mins.

18. The method of claim 11 wherein the delivery system is administered intravenously.

19. The method of claim 11 wherein the subject is irradiated 0-4 h after administering the delivery system.

20. The method of claim 11 wherein the disease is skin carcinoma, esophageal cancer, gastric cancer, eye diseases, or retinoblastoma.

21. A method of making the system of claim 1 wherein the DTAEA is assembled in the presence of DSPE-mPEG to form the nanocarrier.

22. A method of synthesizing (DEAdcCM)$_3$-TAEA (DTAEA), said method comprising the steps of: (i) modifying 7-(diethylamino)-4-(hydroxymethyl)-coumarin (DEACM) photocage having the structure of

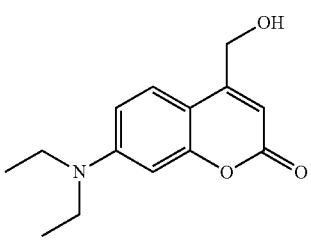

with malononitrile to form dicyanocoumarin (DEAdcCM) having the structure of

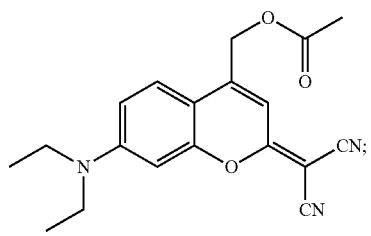
(ii) linking DEAdcCM to TAEA amino groups via a nitrochloroformate-mediated reaction of hydroxyl and amino groups to form DTAEA.
* * * * *